United States Patent [19]
Bachner et al.

[11] Patent Number: 6,140,049
[45] Date of Patent: Oct. 31, 2000

[54] DETECTION AND EARLY DIAGNOSIS OF PROSTATE CANCER

[75] Inventors: Lucien Bachner, Sartrouville; Philippe Berthon, Paris, both of France

[73] Assignee: Genset, Paris, France

[21] Appl. No.: 09/070,106

[22] Filed: Apr. 29, 1998

Related U.S. Application Data

[63] Continuation-in-part of application No. PCT/FR97/02098, Nov. 20, 1997.

[30] Foreign Application Priority Data

Nov. 21, 1996 [FR] France ................................. 96 14245
Apr. 11, 1997 [FR] France ................................. 97 04502

[51] Int. Cl.$^7$ .................................................... C12Q 1/68
[52] U.S. Cl. ........................ 435/6; 435/91.2; 536/24.32; 536/24.31
[58] Field of Search .................. 435/6, 91.2; 536/24.32, 536/24.31

[56] References Cited

FOREIGN PATENT DOCUMENTS

WO 96 20288   6/1996   WIPO .

OTHER PUBLICATIONS

Perkin Elmer Biotechnology Catalog 1992–1993.
Trapman et al. Cancer Research. 54:6061–6064, 1994.
Anbazhagan et al. Amer. J. of Pathology. 152(3): 815–819, Mar. 1998.
MacGrogan et al. Genes, Chromosomes & Cancer. 10:151–159, 1994.
Trybus et al. Cancer Research. 56: 2263–2267, May 1996.
Ittmann. Cancer Research. 56: 2143–2147, May 1996.
Dahiya et al. Int. J. Cancer: 72:283–288, Jul. 1997.
Gyapay et al. Nature Genetics. 7: 246–339, 1994.
Dib et al. Nature. 380:152–154, Mar. 1996.
Egawa, S., et al., "Genomic Instability of Microsatellite Repeats in Prostate Cancer: Relationship to Clinicopathological Variables", Cancer Research 55: 2418–2421 (1995).
Doll, J.A., et al., "Association between prostate cancer in black americans and an allele of the PADPRP locus on chromosome 13", Am. J. Hum. Genet. 58:425–428 (1996).
Van Den Berg, C., et al., "DNA sequences amplification in human prostate cancer identified by chromosome microdissectio: potential prognostic implications", Clin. Cancer Research 1: 11–18 (1995).
Nihei, N., et al., "Localization of Metastasis Suppressor Gene(s) for Rat Prostatic Cancer to the Long Arm of Human Chromosome 10", Genes, Chromosomes & Cancer 14(2): 112–119 (1995).
Smith, J.R., et al., "Major susceptibility locus for prostate cancer on chromosome 1 suggested by a genome–wide search", Science 274: 1371–1374 (1996).
Cooney, K.A., et al., "Prostate cancer susceptibility locus on chromosome 1q: a confirmatory study", J. National Cancer Institute 89(13): 955–959 (1997).
Grönberg, H., et al., "Early stage at diagnosis in families providing evidence of linkage to the hereditary prostate cancer locus (HPC1) on chromosome 1" Cancer Research 57: 4707–4709 (1997).
Carter, B.S., et al., "Mendelian inheritance of familial prostate cancer", Proc. Natl. Acad. Sci., USA 89: 3367–3371 (1992).

*Primary Examiner*—Jeffrey Fredman
*Assistant Examiner*—Juliet C. Einsmann
*Attorney, Agent, or Firm*—Knobbe, Martens, Olson & Bear, LLP

[57] ABSTRACT

The present invention relates to methods for detecting a predisposition or susceptibility to prostate cancer in an individual using microsatellite markers. These markers are located on chromosomes 1, 2, 4, 5, 11 and 13.

10 Claims, 19 Drawing Sheets

| Dnumber | Distances(cM) |
|---|---|
| P | |
| • D1S468 | |
| | (10.20) |
| • D1S214 | |
| | (16.00) |
| • D1S228 | |
| | (15.30) |
| • D1S199 | |
| | (8.90) |
| • DIS234 | |
| | (10.00) |
| • DIS255 | |
| | (11.70) |
| • DIS197 | |
| | (11.00) |
| • DIS220 | |
| | (6.60) |
| • DIS209 | |
| | (11.30) |
| • D1S216 | |
| | (10.40) |
| • D1S207 | |
| | (12.50) |
| • D1S424 | |
| | (7.50) |
| • D1S206 | |
| | (5.70) |
| • <u>D1S248</u> * | |
| | (7.90) |
| • D1S502 | |
| | (3.90) |
| • D1S252 | |
| | (5.60) |
| • D1S498 | |
| | (3.40) |
| • D1S305 | |
| | (9.80) |
| • D1S484 | |
| | (12.50) |
| • D1S196 | |
| | (10.10) |
| • D1S218 | |
| | (10.20) |
| • D1S238 | |
| | (9.80) |
| • D1S413 | |
| | (8.60) |

1A

| | |
|---|---|
| • D1S249 | (10.20) |
| • D1S425 | (0.50) |
| • D1S2703 | (2.70) |
| • D1S2827 | (3.10) |
| • D1S490 | (0.00) |
| • D1S229 | (2.50) |
| • D1S2758 | (2.10) |
| • D1S213 | (1.40) |
| • D1S2631 | (1.40) |
| • D1S251 | (2.20) |
| • D1S2709 | (4.90) |
| • D1S446 | (2.60) |
| • D1S235 | (1.60) |
| • D1S2678 | (9.40) |
| • D1S2785 | (2.30) |
| • D1S321 | (5.30) |
| • D1S2842 | (1.50) |
| • D1S2811 | (3.90) |
| • D1S423 | |

| Dnumber | Distances(cM) |
|---|---|
| D2S2393 | |
| | (7.10) |
| D2S281 | |
| | (9.80) |
| D2S287 | |
| | (10.50) |
| D2S131 | |
| | (2.90) |
| D2S149 | |
| | (6.10) |
| D2S2233 | |
| | (8.80) |
| D2S165 | |
| | (7.60) |
| D2S367 | |
| | (4.50) |
| D2S177 | |
| | (8.60) |
| D2S2174 | |
| | (8.90) |
| D2S2153 | |
| | (0.50) |
| D2S378 | |
| | (9.10) |
| D2S285 | |
| | (8.50) |
| D2S286 | |
| | (1.60) |
| D2S2114 | |
| | (9.60) |
| D2S2161 | |
| | (5.70) |
| D2S113 | |
| | (2.80) |
| D2S2264 | |
| | (9.30) |
| D2S2269 | |
| | (10.90) |
| D2S2215 | |
| | (8.80) |
| D2S114 | |
| | (9.30) |
| D2S151 | |
| | (3.00) |
| D2S2236 | |
| | (11.10) |
| D2S156 | |
| | (12.00) |

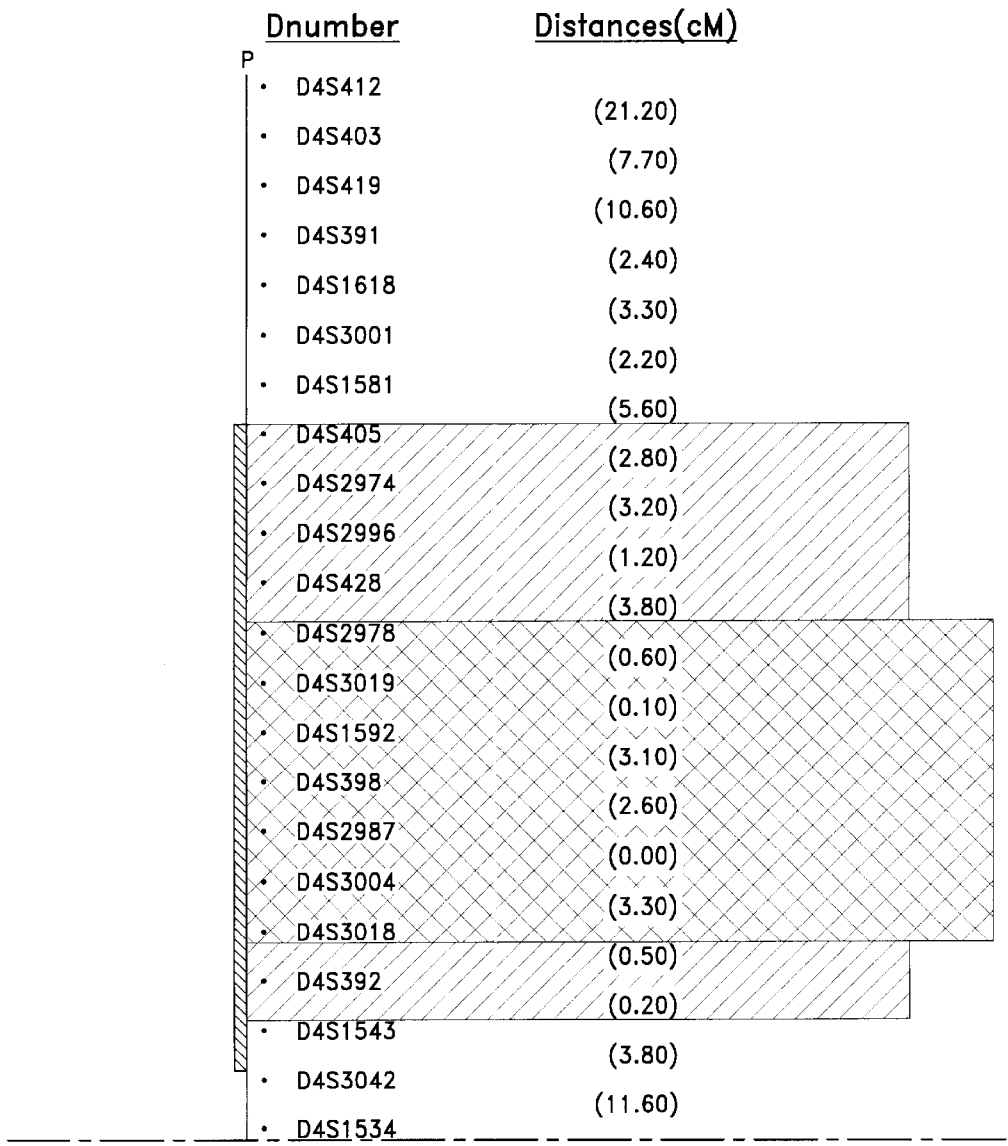

| FIG. 4A |
|---|
| FIG. 4B |

| Dnumber | Distances(cM) |
|---|---|
| D5S392 * | (10.70) |
| D5S406 | (7.90) |
| D5S630 | (9.30) |
| D5S416 * | (11.60) |
| D5S419 | (12.10) |
| D5S426 * | (6.50) |
| D5S418 | (1.80) |
| D5S822 | (1.20) |
| D5S1969 | (2.70) |
| D5S645 | (0.10) |
| D5S2068 | (1.10) |
| D5S407 * | (2.20) |
| D5S2102 | (1.80) |
| D5S2107 | (1.60) |
| D5S1990 | (3.30) |
| D5S2072 | (0.80) |
| D5S647 | (1.80) |
| D5S2019 | (2.50) |
| D5S1988 | (3.80) |
| D5S424 * | (12.60) |
| D5S428 | (9.10) |
| D5S644 | (3.30) |
| D5S495 * | (4.40) |
| D5S433 | |

FIG. 7

| Dnumber | Distances(cM) |
|---|---|
| P | |
| D11S922 | |
| | (11.70) |
| D11S1338 | |
| | (5.70) |
| D11S1349 * | |
| | (4.10) |
| D11S902 | |
| | (12.30) |
| D11S904 | |
| | (12.60) |
| D11S935 | |
| | (6.10) |
| D11S905 | |
| | (3.80) |
| D11S903 * | |
| | (3.70) |
| D11S1313 | |
| | (14.30) |
| D11S1314 | |
| | (2.60) |
| D11S916 * | |
| | (4.50) |
| D11S937 | |
| | (5.20) |
| D11S901 | |
| | (6.50) |
| D11S1332 * | |
| | (0.00) |
| D11S1358 | |
| | (6.80) |
| D11S898 | |
| | (5.60) |
| D11S927 | |
| | (3.80) |
| D11S908 | |
| | (0.10) |
| D11S1885 | |
| | (6.00) |
| D11S1306 | |
| | (7.40) |
| D11S1345 | |
| | (3.50) |
| D11S4094 | |
| | (2.20) |
| D11S934 * | |
| | (15.50) |
| D11S1320 | |
| | (5.60) |
| D11S968 * | |
| Q | |

FIG. 8

| Dnumber | Distances(cM) |
|---|---|
| P | |
| D13S217 | |
| | (8.20) |
| D13S171 * | |
| | (13.10) |
| D13S263 | |
| | (7.10) |
| D13S153 | |
| | (0.10) |
| D13S284 * | |
| | (9.70) |
| D13S156 | |
| | (2.40) |
| D13S162 | |
| | (1.20) |
| D13S1281 | |
| | (1.80) |
| D13S160 | |
| | (2.70) |
| D13S170 * | |
| | (1.10) |
| D13S1264 | |
| | (1.20) |
| D13S1290 | |
| | (0.80) |
| D13S1283 | |
| | (1.20) |
| D13S1230 | |
| | (0.80) |
| D13S1234 | |
| | (0.10) |
| D13S265 | |
| | (2.50) |
| D13S1300 | |
| | (1.20) |
| D13S281 | |
| | (1.50) |
| D13S167 | |
| | (1.30) |
| D13S154 | |
| | (4.40) |
| D13S1298 | |
| | (0.00) |
| D13S159 | |
| | (2.20) |
| D13S1240 | |
| | (3.20) |
| D13S158 * | |
| | (0.60) |
| D13S280 | |
| | (8.40) |
| D13S173 | |
| | (0.00) |
| D13S286 | |
| | (16.90) |
| D13S285 | |
| Q | |

DETECTION AND EARLY DIAGNOSIS OF PROSTATE CANCER

RELATED APPLICATIONS

The present application is a continuation-in-part of PCT/FR 97 02098, filed Nov. 20, 1997, which claims priority from French Patent Application Serial No. 96 14245, filed Nov. 21, 1996, and French Patent Application 97 04502 filed Apr. 11, 1997.

BACKGROUND OF THE INVENTION

The present invention relates especially to the familial detection of predisposition or susceptibility to prostate cancer, as well as to the possibility of demonstrating the genes responsible for this disease, and the therapeutic strategies derived from this identification.

In France, the rough rate of incidence of prostate cancer is 35/100,000 men. This rate increases regularly by 10/100,000 per decade. In parallel, mortality from prostate cancer progresses: 8234 deaths or 10% of the deaths from cancer in 1986, and 9000 or 11% in 1990. The estimations, in terms of public health, are pessimistic for prostate cancer because of the ageing of the population; this cancer is the 2nd cause of mortality from cancer in man and the 1st in men of more than 70 years.

The study of the natural history of prostate cancers shows that men having prostate cancer on average lose 40% of their life expectancy. At present, the only curative treatments of prostate cancer in its localized (early) form are surgery or radiotherapy, with a recovery rate at 5 years limited to approximately 50%. In order that the mortality rate from this cancer decreases, more localized tumours must be detected because these are, in the state of therapeutics available, the only ones which are curable.

Early diagnosis based on the determination of PSA (prostate specific antigen) appears to be the method today which is most able to contribute to a decrease in mortality from prostate cancer: the rise in the level of PSA will precede clinical detection for the localized forms by approximately 7 years. However, certain reserves have been expressed with respect to the use of the determination of PSA for detecting prostate cancers; in fact, the PSA level is not specific for prostate cancer, but for a pathological attack on this organ, whether it be benign or malignant.

A predictive diagnosis by genetic means must allow the susceptible individuals to benefit from a more early and thus curative treatment, or even from a non-specific chemoprevention (retinoic acid, vitamin D or 5α-reductase inhibitors) or specific chemoprevention, made practicable from the identification of the genetic bases of the disease.

It is thus important to be able to define with accuracy the populations at risk of prostate cancer in order to be able to apply a rational detection and early diagnosis strategy, on the data of the predictive genotype diagnosis.

However, the risk factors of prostate cancer in general populations are not at present known with certainty.

The incidence of clinical prostate cancer varies according to the countries and the ethnic groups; to explain these variations, genetic and epigenetic factors, have been touched on without it having been possible to incriminate any mesological factor with an absolute significance. The standardized incidence (for 100,000 inhabitants) of clinical prostate cancer is estimated at 35 in France, but the figures vary from 2 in China to 80 for the dark-skinned population in the USA.

No etiological cause of alimentary origin or connected with the environment has been determined with certainty to this date.

Certain genetic polymorphisms are associated with an increased individual risk of specific cancers, and in the case of prostate cancer could explain the significant variations in incidence observed between different populations. A specific polymorphism of the black American populations which have a high risk of prostate cancer has been demonstrated for the gene of the enzyme 5α-reductase of type 2 (SRD5A2 gene localized in 2p23). The 5α-reductase of type 2 is an enzyme which transforms testosterone into dihydrotestosterone and which is directly involved in growth and androgen-dependent prostate differentiation. Independently of the ethnic origin, a specific polymorphism of the gene of the vitamin D receptor (VDR gene localized in 12q12) has been correlated with a risk of developing prostate cancer; it had additionally been suggested that the individuals having a low circulating level of vitamin D were more exposed to prostate cancer.

It is known today that there is a familial risk of prostate cancer. Already, clinical studies in the 1950s had caused a familial aggregation in prostate cancer to be recalled. Control-case clinical studies have been conducted more recently to attempt to evaluate the part of the genetic risk factors. Thus Steinberg et al., 1990, and McWhorter et al., 1992 confirm that the risk of prostate cancer is increased in subjects having one or more relatives already affected by the disease and when forms of early diagnosis in the relatives exist.

It follows from these studies that previous familial histories of prostate cancer are the principal risk factor of prostate cancer. It is thus essential to be able to identify the genetic bases of these susceptibilities or predispositions to prostate cancer in order to be able to target the individuals who can benefit from a diagnosis and a more efficacious treatment.

Genetic analyses (research on loss of heterozygosis and of point mutations) have been conducted in prostate tumours.

It is now well established that cancer is a disease due to the deregulation of the expression of certain genes. In fact, the development of a tumour necessitates an important succession of steps. Each of these steps comprises the deregulation of an important gene intervening in the normal metabolism of the cell and the emergence of an abnormal cellular sub-clone which overwhelms the other cell types because of a proliferative advantage. The genetic origin of this concept has found confirmation in the isolation and the characterization of genes which could be responsible. These genes, commonly called "cancer genes", have an important role in the normal metabolism of the cell and are capable of intervening in carcinogenesis following a change.

The studies of loss of heterozygosis (LOH) in the DNA of tumours and cytogenetic observations have shown that several chromosomal regions were lost in certain prostate cancers. No cytogenetic change, no oncogene, nor specific predisposition gene, however, has yet been identified as specific for prostate cancers (review by Cussenot, 1996). The research is carried out by observation of certain deletions or losses of alleles on cancers in different clinicopathological stages. Certain of these deleted chromosomal regions are already known to be carriers of suppressor genes of tumours involved in different cancers and thus do not have any specificity in prostate adenocarcinomas (13q-14 and Rb gene, 18q-21 and DCC gene, 16q22 and E-caderine gene, 17q-13 and p53 gene, 17q-12 and BRCAI gene). The KAI1 gene (11p11.2) has been identified for the first time as a suppressor gene of prostate cancer metastasis; this gene is expressed in numerous tissues, it codes for a membrane glycoprotein, and its suppressant function which is restricted to prostate cancers does not remain very probable. The oncogenes and genetic amplifications observed in the prostate cancers would appear to be involved in a late state of the disease, in particular during the escape phase in hormonal treatment.

It thus remains to localize and to identify the genes specifically involved in the development and the progression of prostate cancers starting from the genetic analysis of the hereditary forms and to define their clinical implications in terms of prognosis and therapeutic innovations.

BRIEF DESCRIPTION OF THE DRAWINGS

The attached figures show:

FIG. 1: positioning of the microsatellite markers of interest carried by chromosome 1

Figure 2B:
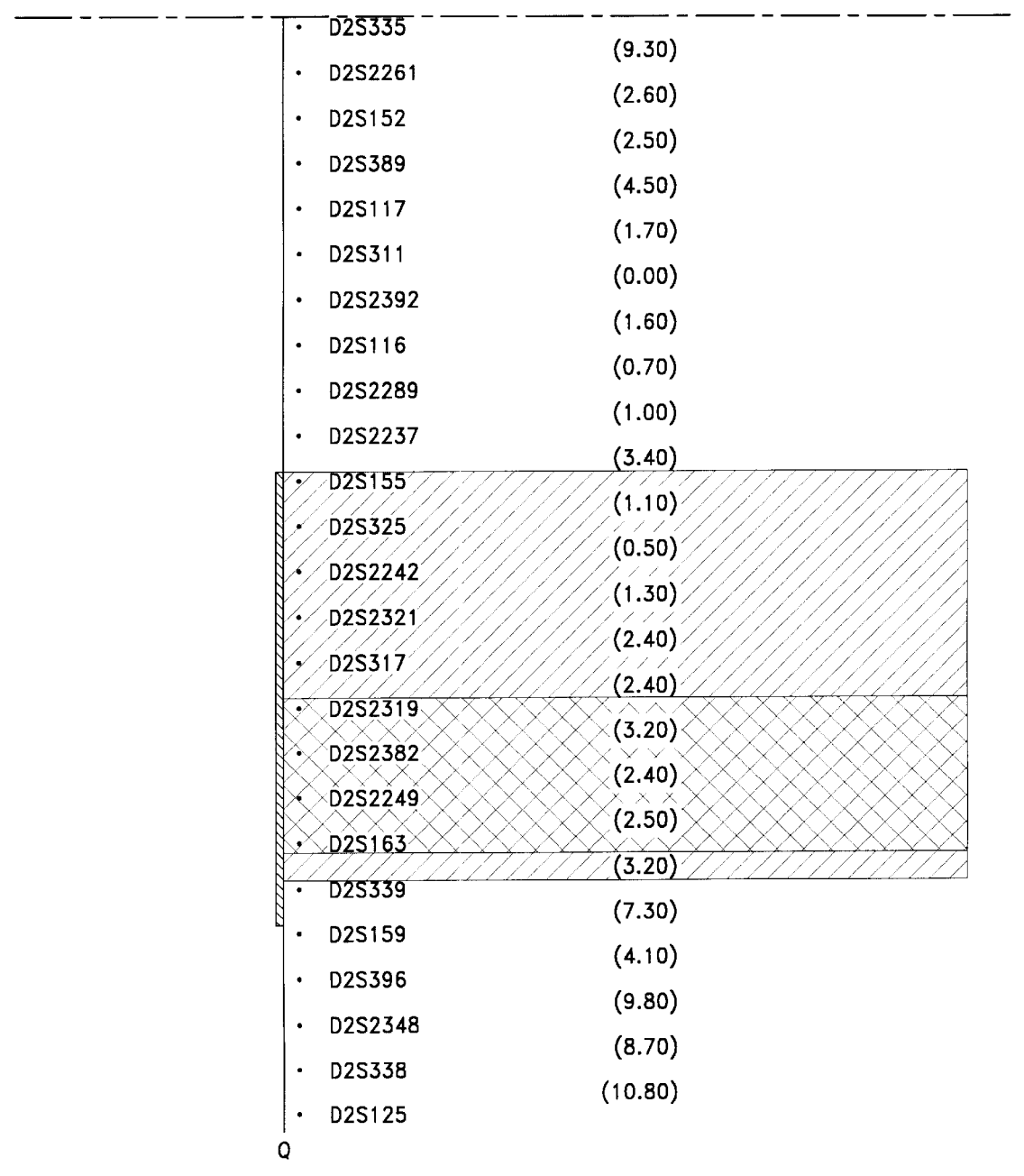

FIG. 2: positioning of the microsatellite markers of interest carried by chromosome 2

Figure 3B:
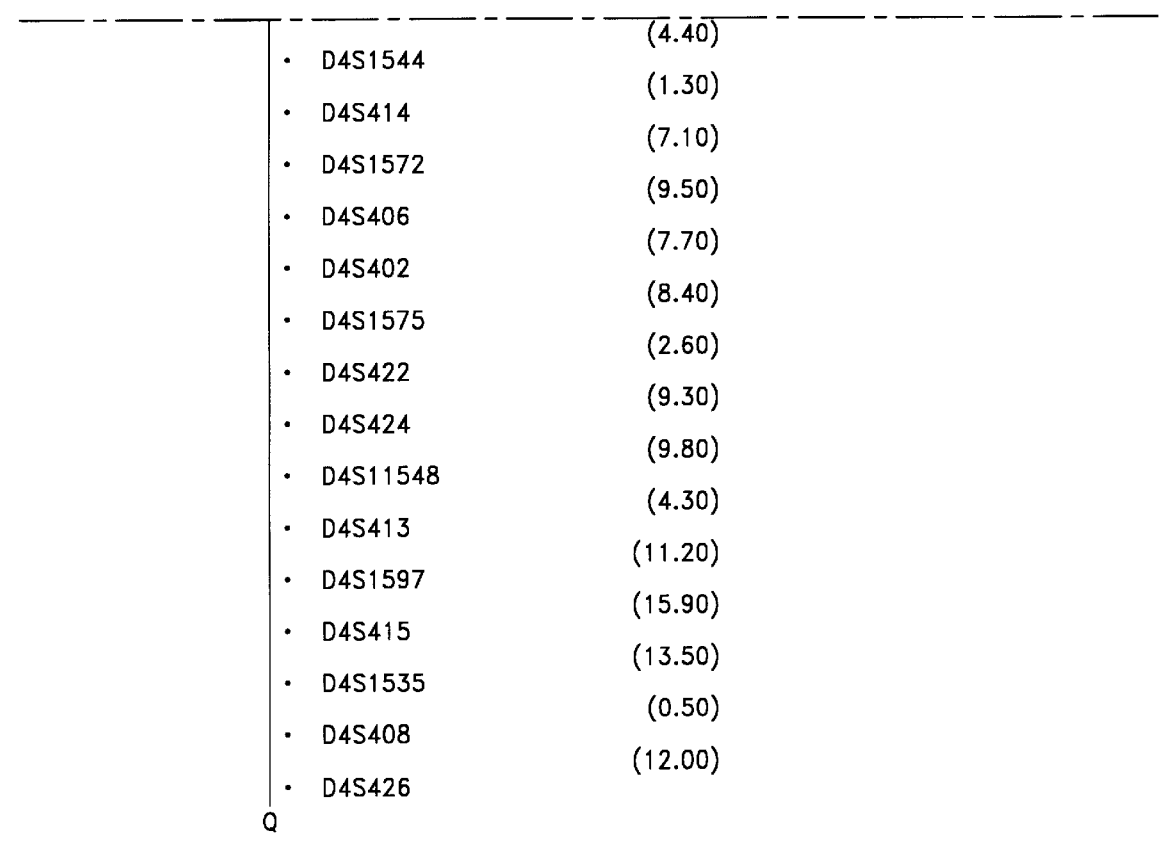

FIG. 3: positioning of the microsatellite markers of interest carried by chromosome 4

FIG. 7: positioning of the microsatellite markers of interest carried by chromosome 11

FIG. 8: positioning of the microsatellite markers of interest carried by chromosome 13

For all of FIGS. 1 to 8:

Dnumber: marker of interest in two-point analysis on a dataset of 18 families (progene study 1) or on about fifty families (progene study 2)

(*): panel of markers of progene study 1, genotypes on 18 families (certain markers also appear in the progene sample group 1, genotypes on about fifty families).

Figure 4B:
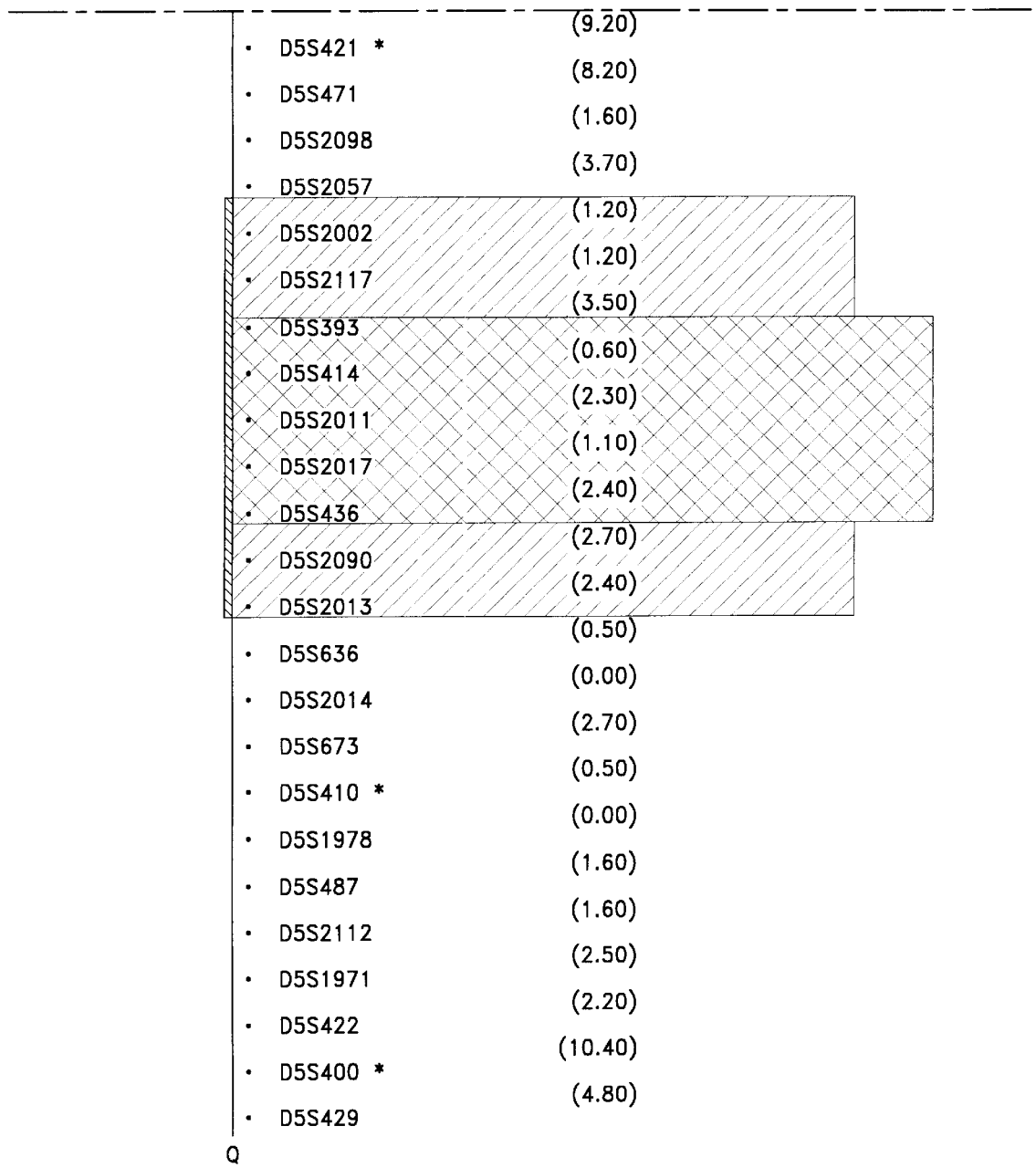
FIG. 4: positioning of the microsatellite markers of interest carried by chromosome 5
Figure 5:
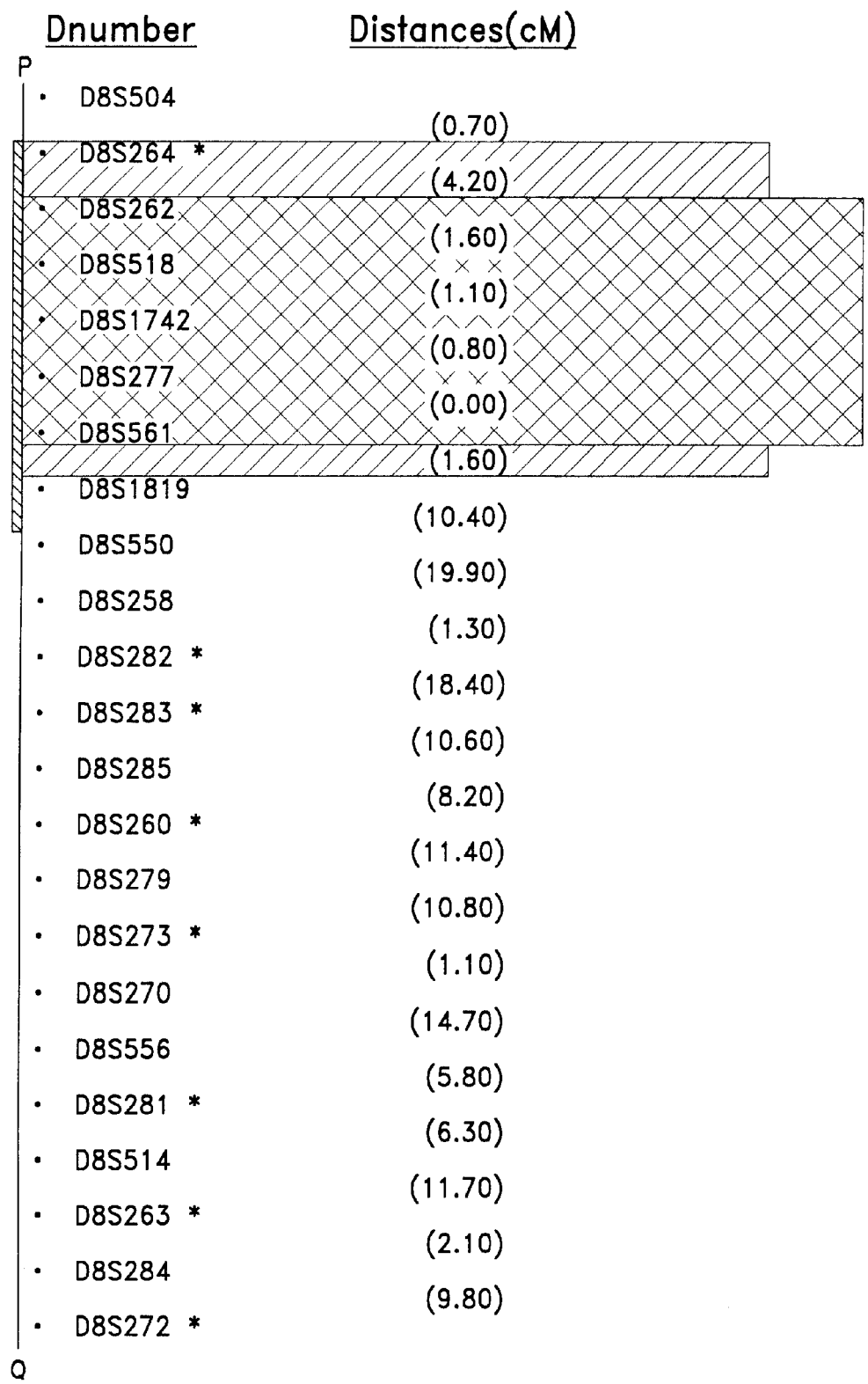
FIG. 5: positioning of the microsatellite markers of interest carried by chromosome 8
Figure 6:
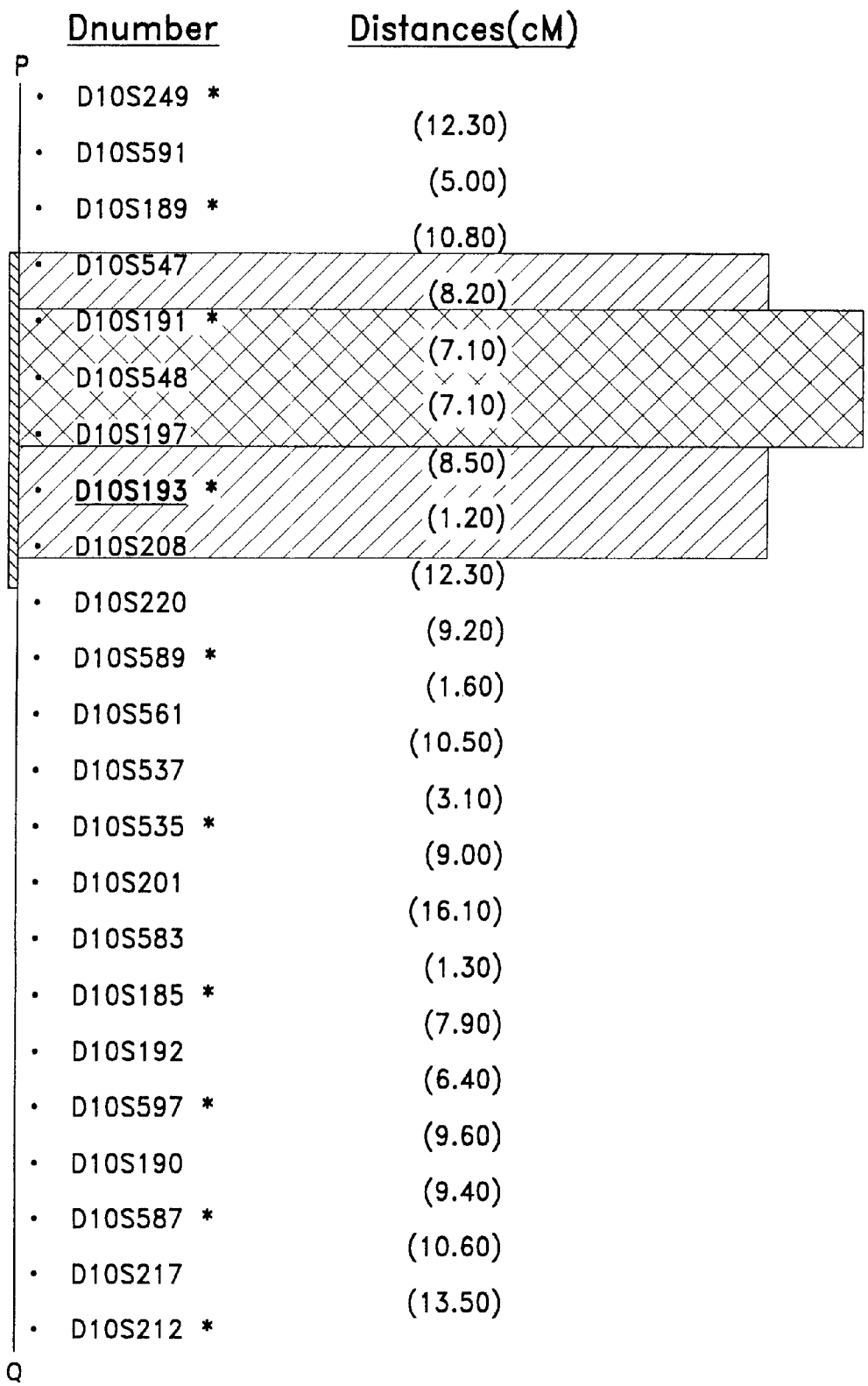
FIG. 6: positioning of the microsatellite markers of interest carried by chromosome 10
Figure 9:
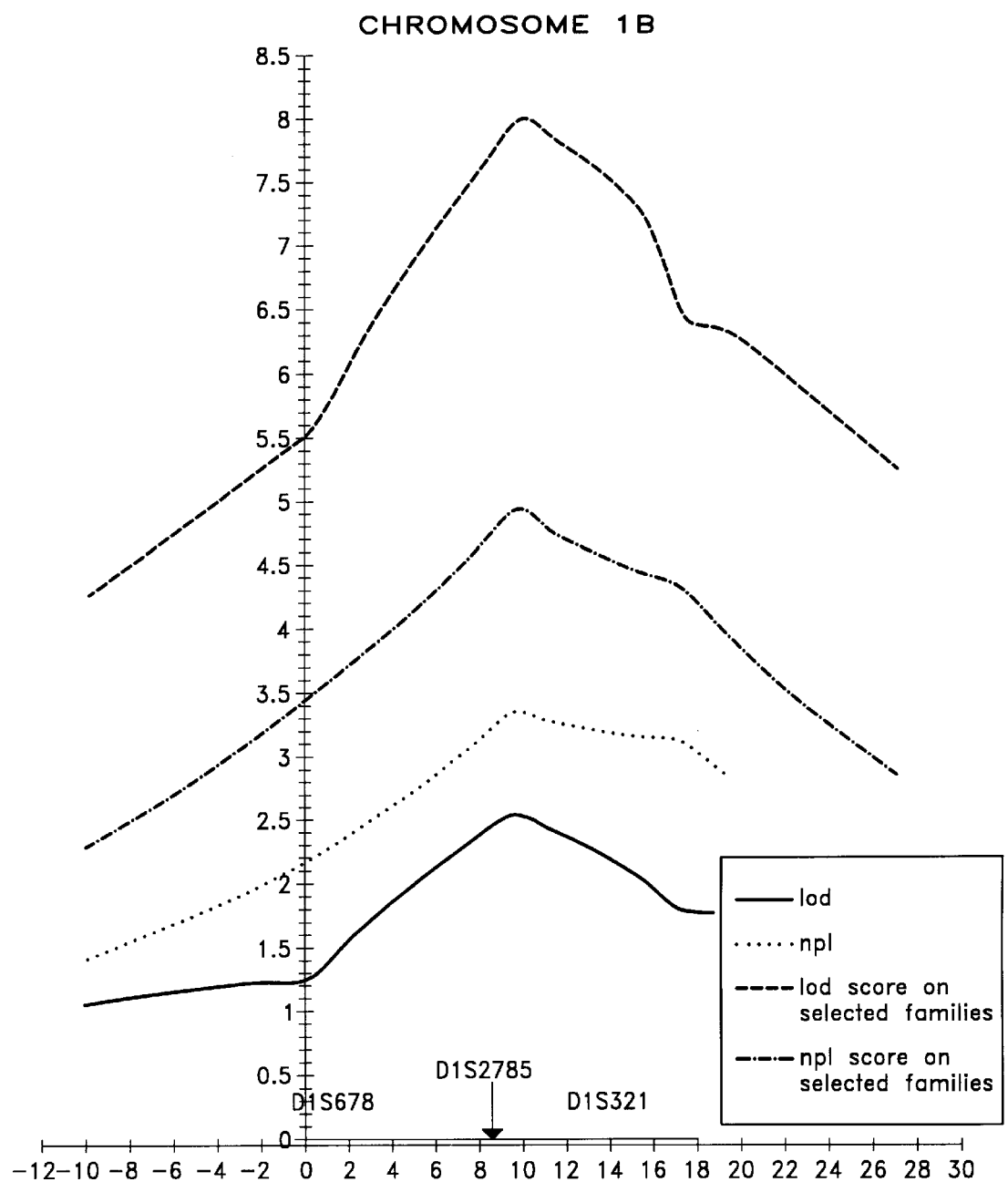
Figure 10:
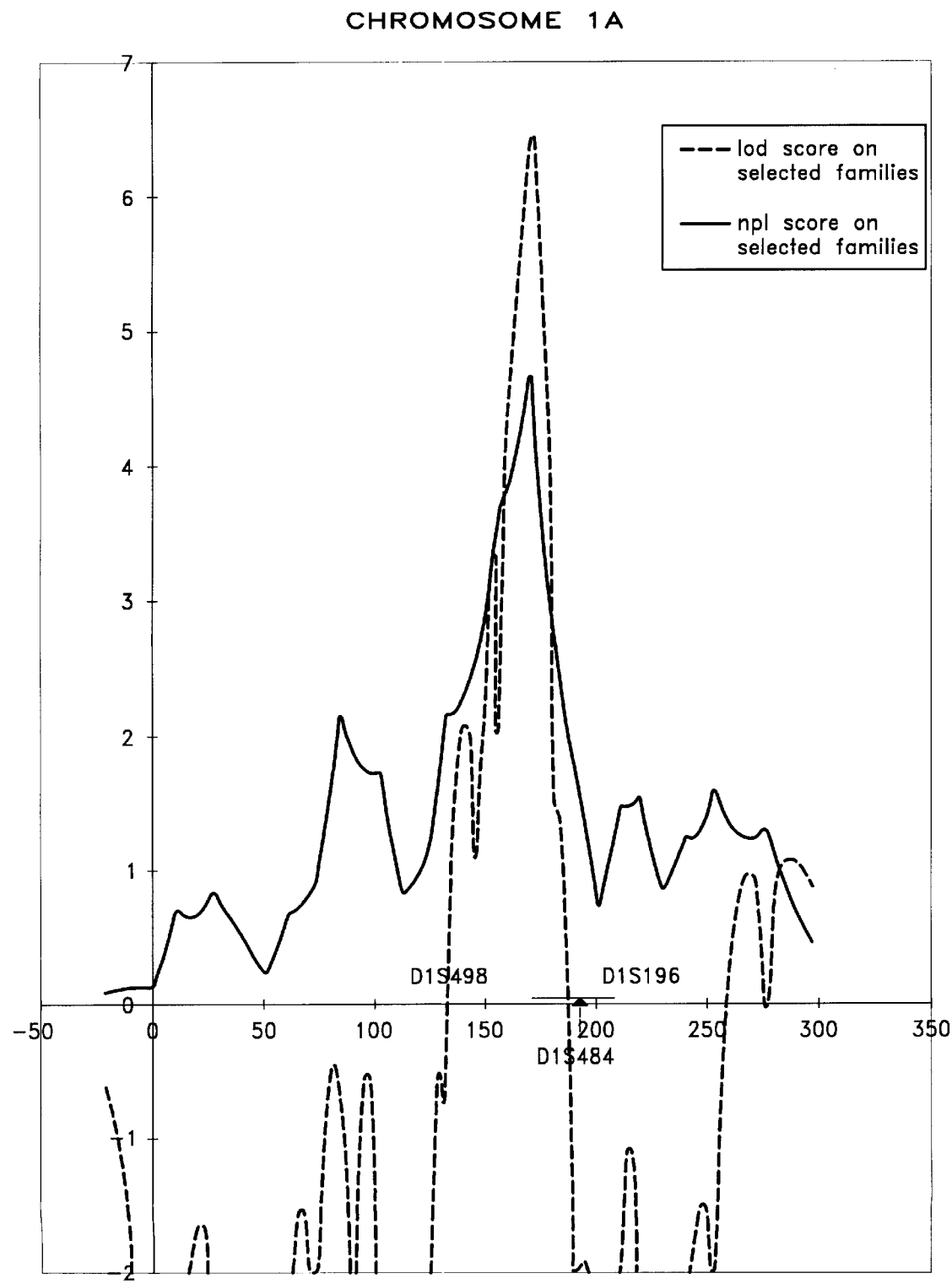
Figure 11:
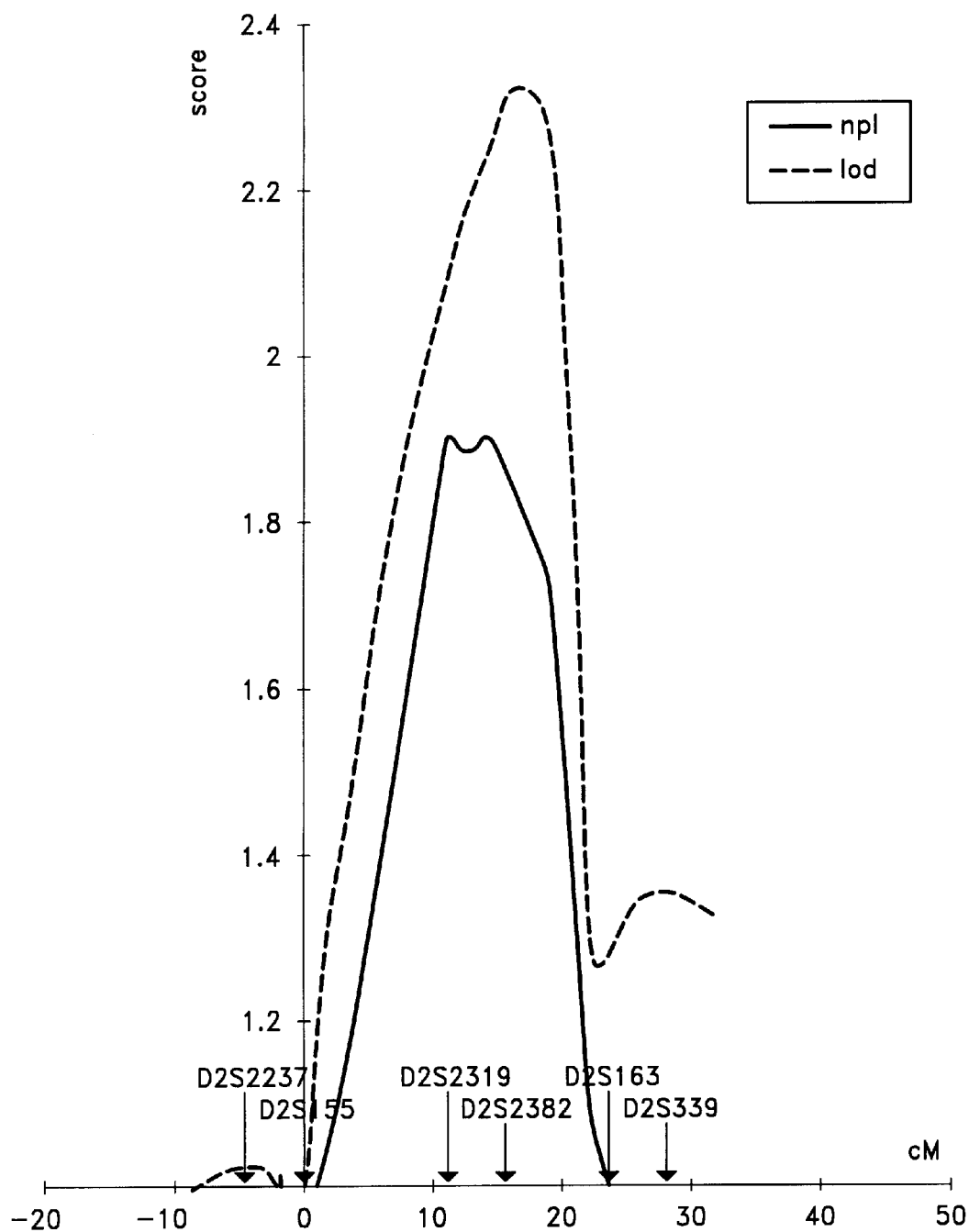

FIG. 9: variation of the lod score obtained during genetic analysis corresponding to the markers carried by chromosome 1, region 1B FIG. 10: variation of the lod score obtained during genetic analysis corresponding to the markers carried by chromosome 1, region 1A FIG. 11: variation of the lod score obtained during genetic analysis corresponding to the markers carried by chromosome 2

Figure 12:
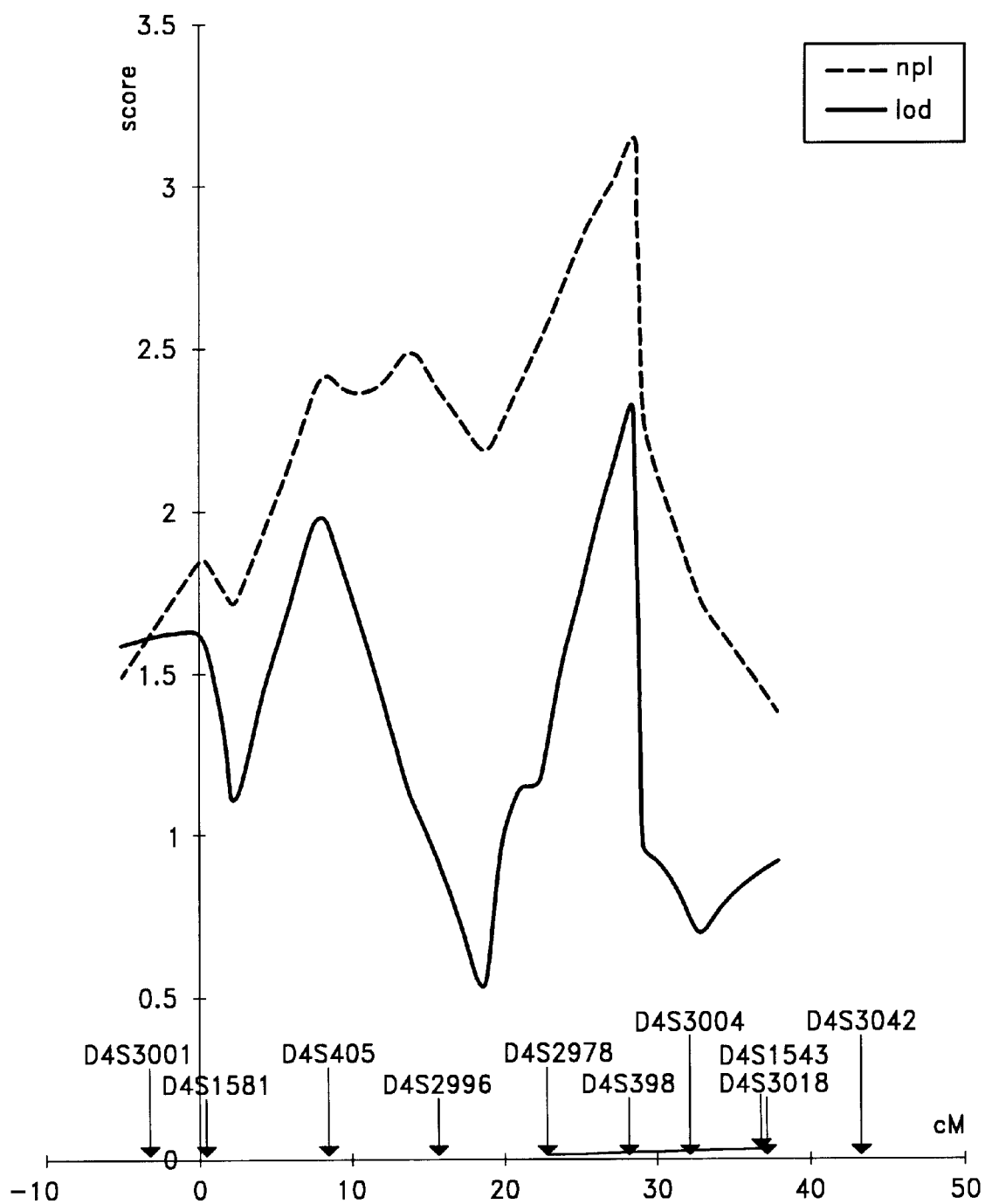

FIG. 12: variation of the lod score obtained during genetic analysis corresponding to the markers carried by chromosome 4

Figure 13:
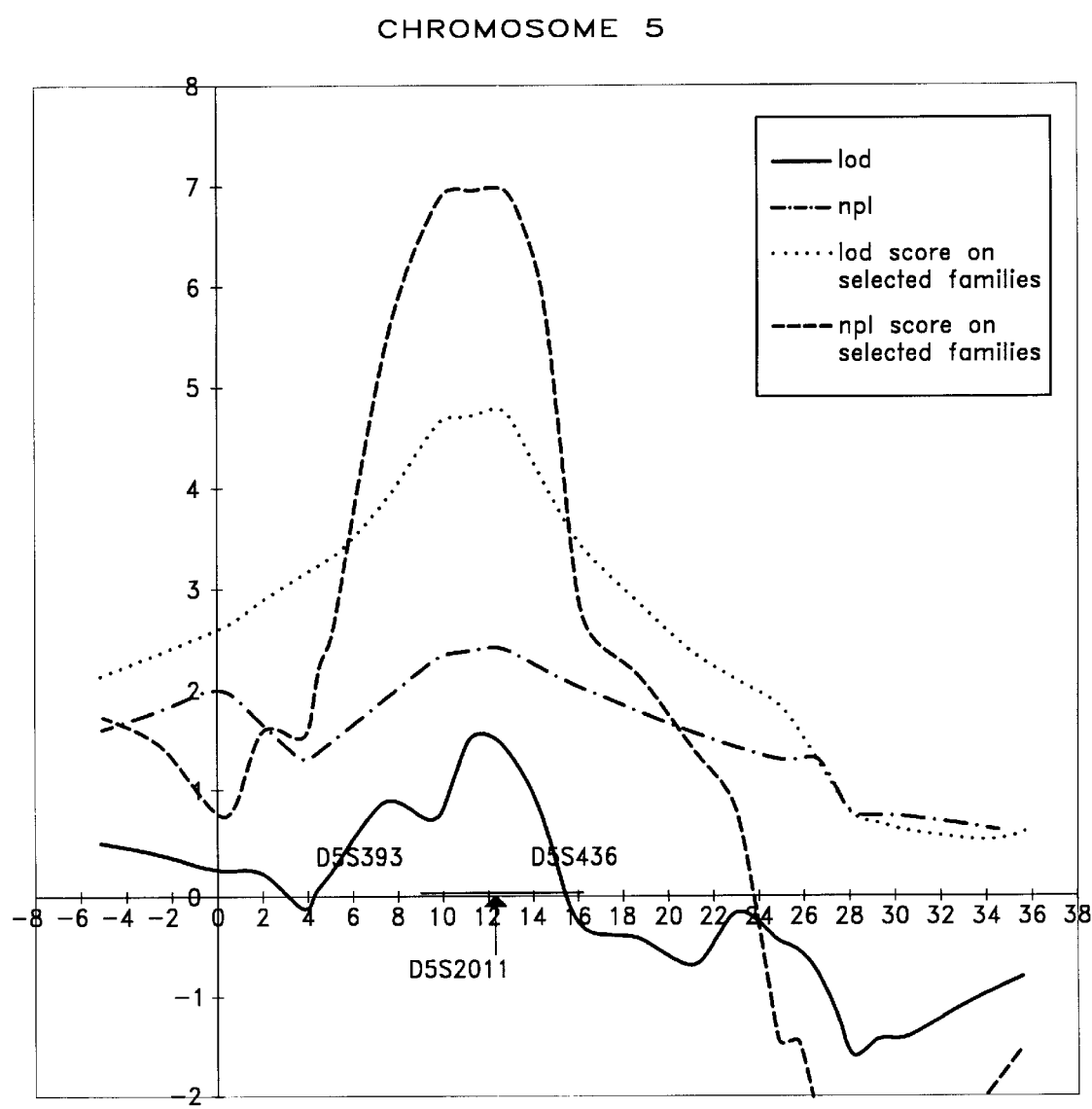

FIG. 13: variation of the lod score obtained during genetic analysis corresponding to the markers carried by chromosome 5

Figure 14:
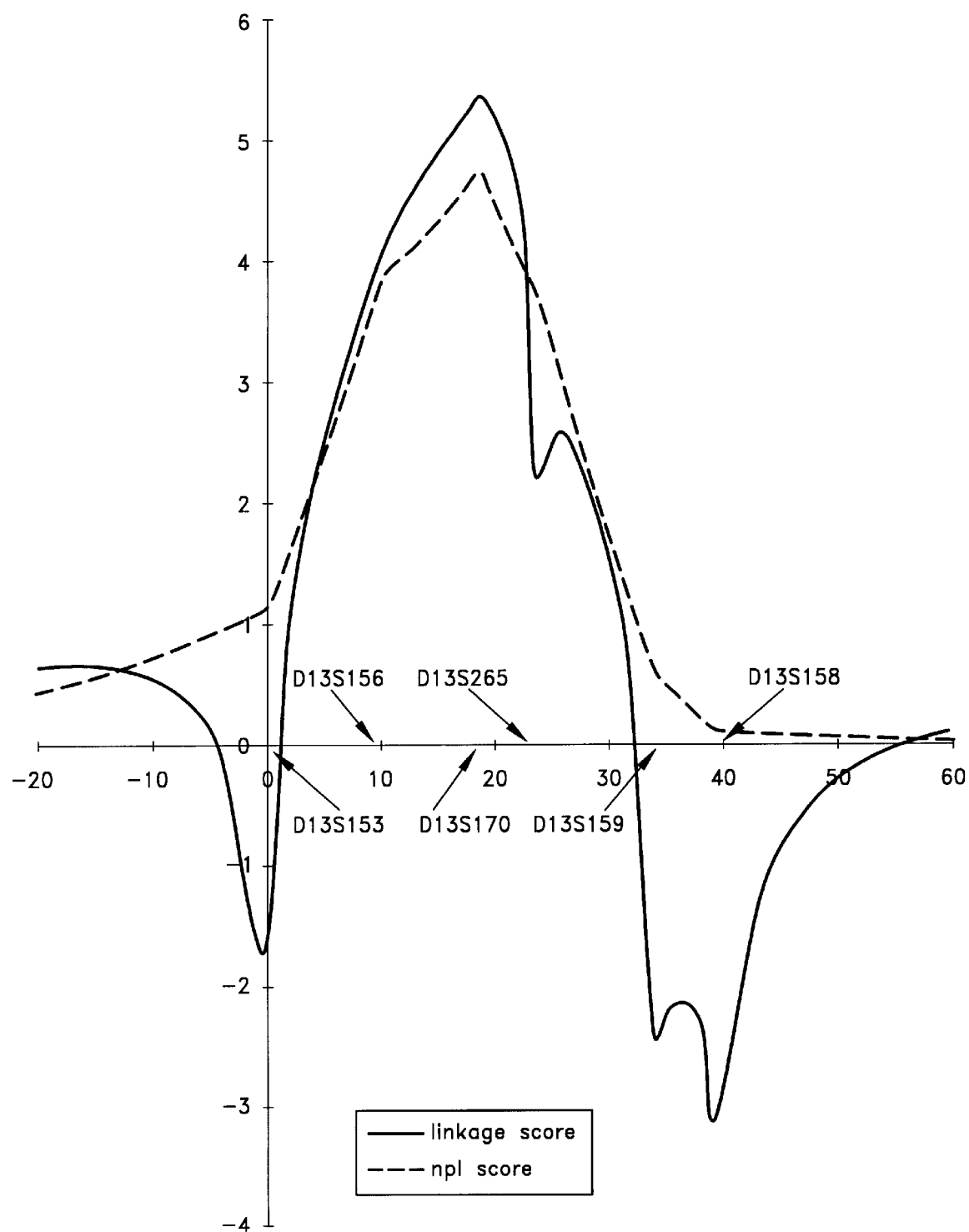

FIG. 14: variation of the lod score obtained during genetic analysis corresponding to the markers carried by chromosome 13

Figure 15:
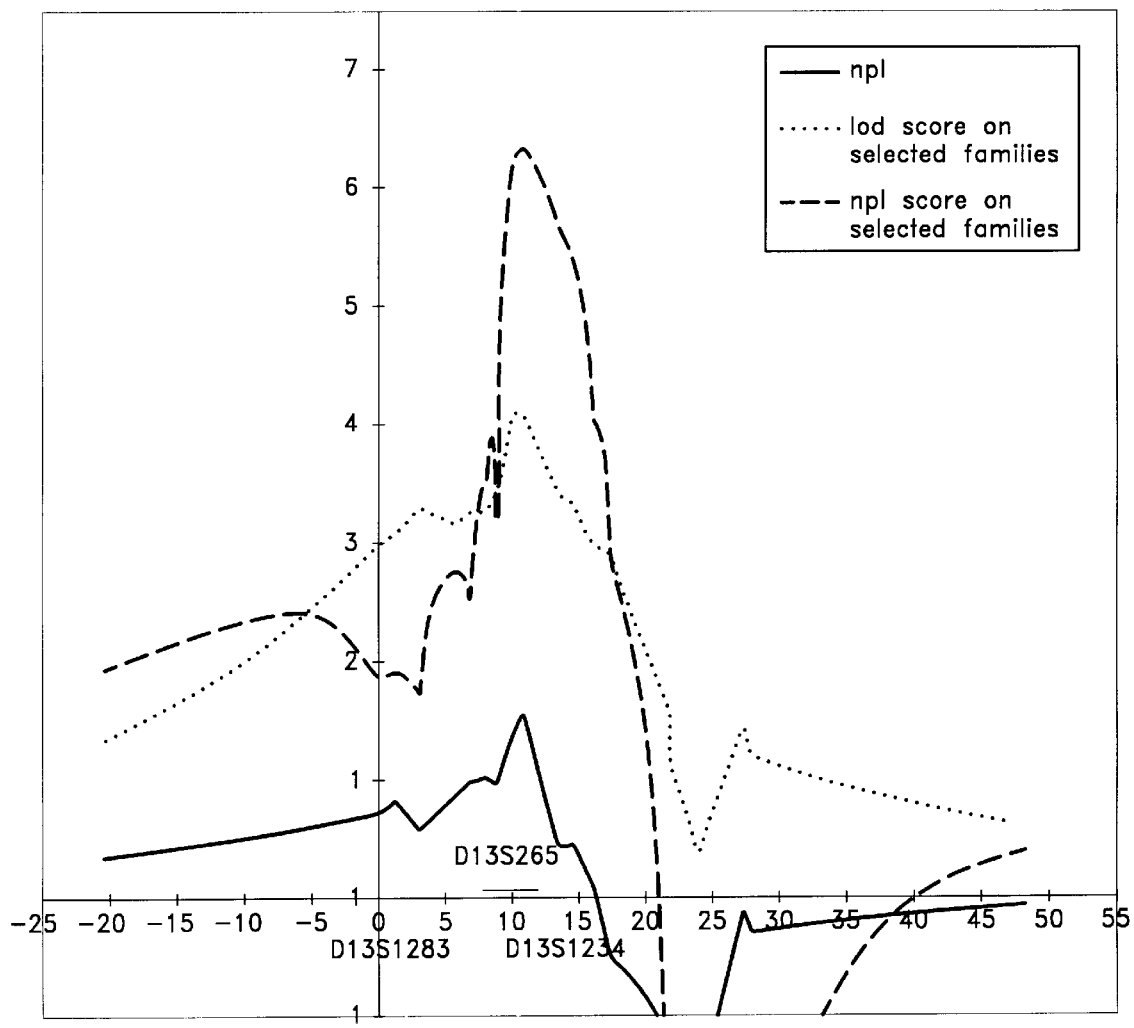

FIG. 15: variation of the lod score obtained during "fine" genetic analysis corresponding to the markers carried by chromosome 13

For all of FIGS. 9 to 15:

"lod" and "npl" represent the lod score and npl score calculated on all of the families (i.e. about fifty)

"lod on selected families" and "npl on selected families" represent the lod score and npl score calculated on a subtotal of families having a high probability of link to the locus considered.

[FIG. 10: 23 families selected

FIG. 13:19 families selected

FIG. 14: 20 families selected].

DETAILED DESCRIPTION OF THE PREFERRED EMBODIMENT

The study of hereditary cancers is at the origin of the discovery of prostate cancer suppressor genes in its familial and sporadic forms. The function of the genes discovered is not limited to a suppressant function stricto sensu but may correspond to an activity of oncogenic type as has been shown for predisposition to multiple neuroendocrine tumours; these genes code especially for oncoproteins corresponding to growth factors, membrane receptors of growth factors, membrane proteins binding GTP, membrane protein kinases, cytosolic protein kinases, mitochondrial proteins, nuclear proteins or transcription factors and nuclear receptors. The susceptibility genes may count among the metabolism genes of exogenous carcinogens, the genes of the DNA repair systems or genes which intervene in resistance to the treatments (resistance genes to chemotherapy or to androgenodepletion) as is the case for the genes involved in the apoptosis phenomenon which, altered, would cause an inequilibrium between proliferation and programmed cell death and would give rise to the appearance of a tumour clone and then to the growth of a tumour.

The suppressor genes play an important part in the negative control of cell growth. Several proven or potential suppressor genes code for internal organization molecules of the cell or for molecules ensuring adhesion with other cells or with the extracellular medium.

The identification of the genetic bases of prostate cancer is thus necessary for:

(i) the development of genotype diagnosis methods which allow a predictive diagnosis in asymptomatic subjects.

When the deleterious gene, still unknown, is localized due to a DNA proximity marker (microsatellite marker for example): analysis of the case index, of his parents, of his brothers and sisters, or even of his grandparents allows the individuals to be identified in each family who have inherited the allele of a marker linked to the disease gene in the family.

When the gene is identified (cloned and sequenced) and the mutations recognized: diagnosis can be made by direct recognition of the mutation in question in the family.

(ii) the development of a novel therapeutic strategy where the identification of the susceptibility genes or of predisposition to prostate adenocarcinomas in certain population groups or in certain families is bound to allow subjects at risk to be distinguished at the individual level by a genotype diagnosis method. In practice, the individuals concerned could benefit from a close surveillance in order to discover earlier forms of prostate cancer, to improve the prognosis thereof, or even to contemplate a chemoprevention.

(iii) The development of novel therapeutic methods by identifying the expression product of these genes to restore a functional homeostasis.

In order to localize the familial prostate cancer gene(s) starting from families, a systematic familial study of genetic link research is carried out using the markers of microsatellite type described at the Genethon laboratory by the Jean Weissenbach team (Dib et al., 1996). The markers used in the methods of the present invention are described in Dib et al., Nature 1996, 380: III–V, the disclosure of which is incorporated herein by reference.

The studies of genetic link or of "linkage" are based on the principle according to which two neighboring sequences on a chromosome do not present (or very rarely present) recombinations by crossing-over during meiosis. To do this, microsatellite DNA sequences (chromosomal markers) constantly co-inherited with the disease studied are searched for in a family having a predisposition. These DNA sequences organized in the form of repetition of di-, tri- or tetranucleotides are systematically present all along the genome, and thus allow the identification of chromosomal fragments by intermediacy. These nucleotide sequences, or microsatellite markers, have been localized with precision on the genome (more than 5000 markers) due to the first work on the genetic map carried out at Genethon under the supervision of Jean Weissenbach, and on the physical map (using the "Yeast Artificial Chromosomes"), work conducted by Daniel Cohen at C.E.P.H. and at Genethon (Chumakov et al., 1995). Genetic link analysis calculates the probabilities of recombinations of the target gene with the chromosomal markers used, according to the genealogical tree, the transmission of the disease, and the transmission of the markers. Thus if a particular allele of a given marker is transmitted with the disease more often than chance would have it (recombination level of between 0 and 0.5), it is possible to deduce that the gene in question is found in the neighborhood of the marker. It has thus been possible to localize several genes of genetic predisposition to familial cancers. In order to be able to be included in a genetic link study, the families affected by a hereditary form of the disease must satisfy the "informativeness" criteria: several affected subjects (and whose constitutional DNA is available) per generation, and at the best belonging to large sibships.

The present invention thus relates to a detection procedure for predisposition or susceptibility to prostate cancer in an individual, characterized in that, in a biological sample from the said individual, the presence of alleles of markers linked to the occurrence of prostate cancer in his family is detected, these markers being chosen from the microsatellite markers included in one of the nine following groups of markers;

D1S235, D1S2678, D1S2785, D1S321, D1S2842 of chromosome 1

D1S252, D1S498, D1S305, D1S484, D1S196, D1S218 of chromosome 1

D2S155, D2S325, D2S2242, D2S2321, D2S317, D2S2319, D2S2382, D2S2249, D2S163, D2S339 of chromosome 2

D4S405, D4S2974, D4S2996, D4S428, D4S2978, D4S3019, D4S1592, D4S398, D4S2987, D4S3004, D4S3018, D4S392, D4S1543 of chromosome 4

D5S2002, D5S2117, D5S393, D5S414, D5S2011, D5S2017, D5S436, D5S2090, D5S2013 of chromosome 5

D8S264, D8S262, D8S518, DSS1742, D8S277, D8S561, D8S1819 of chromosome 8

D10S547, D10S191, D10S548, D10S197, D10S193, D10S208 of chromosome 10

D11S898, D11S927, D11S908, D11S1345, D11S934, D11S1320 of chromosome 11

D13S1290, D13S1283, D13S1230, D13S1234, D13S265, D13S1300, D13S281 of chromosome 13 and the polymorphic markers situated inside regions defined by the above markers.

"Polymorphic marker" is understood as meaning any Mendelian character sufficiently polymorphic able to be used as a genetic marker. Among the DNA polymorphisms identified up to now in man, the following are especially counted:

RFLPs (restriction fragment length polymorphism): polymorphisms concerning a nucleotide and modifying an enzymatic restriction site; in a number greater than 100,000, they can be analysed by PCR; they are biallelic markers (the restriction site is present, or it is absent); they form the first generation of genetic markers.

VNTRs (variable number tandem repeat):

minisatellites: series of moderate size of DNA sequences repeated in tandem, dispersed over considerable portions of the nuclear genome (from 0.1 to 20 kb); in a number greater than 10,000 they are identified by Southern blotting, and are highly polymorphic (numerous alleles possible), and thus informative.

microsatellites: small series of repeated single sequences in tandem (especially di-, tri-, tetranucleotides), dispersed over all the genome; among the 10,000 potential microsatellite VNTRs, 5000 are analysable by automated multiplex PCR; they are highly polymorphic and thus informative; the VNTRs form the present generation of most-used genetic markers.

Biallelic markers concerning a nucleotide: polymorphisms concerning a sole nucleotide-the RFLPs are a subpart thereof; in a number potentially greater than 1 million, they can be analysed by numerous techniques (sequencing, hybridization . . . ); their informativeness is limited by the fact that they are biallelic, but this disadvantage can be overcome by the concomitant analysis of two or three contiguous biallelic markers.

More precisely, the following will be used for this detection procedure:

Any polymorphic marker situated on chromosome 1 in the region encoded by the markers D1S2678 and D1S321.

Any polymorphic marker situated on chromosome 1 in the region encoded by the markers D1S498 and D1S196.

Any polymorphic marker situated on chromosome 2 in the region encoded by the markers D2S2319 and D2S163.

Any polymorphic marker situated on chromosome 4 in the region encoded by the markers D4S2978 and D4S3018.

Any polymorphic marker situated on chromosome 5 in the region encoded by the markers D5S393 and D5S436.

Any polymorphic marker situated on chromosome 8 in the region encoded by the markers D8S262 and D8S561.

Any polymorphic marker situated on chromosome 10 in the region encoded by the markers D10S191 and D10S197.

Any polymorphic marker situated on chromosome 11 in the region encoded by the markers D11S908 and D11S934.

Any polymorphic marker situated on chromosome 13 in the region encoded by the markers D13S1283 and D13S1300.

The relative positions of the microsatellite markers previously mentioned on each of the corresponding chromosomes are shown in FIGS. 1 to 8.

The techniques employed for detecting the presence of markers are known; they can consist especially of direct detection with the aid of a probe complementary to the marker, but the methods employing an amplification of the marker sequence will preferably be used, for example by PCR-type methods with the aid of primers of which one is labelled by cold labelling, such as a fluorochrome, or is unlabeled.

The present invention likewise relates to a diagnostic kit intended to be employed for the preceding detection procedure.

As has been indicated previously, the presence of an allele of at least one of the markers identified previously which are linked to the occurrence of the disease in the family, indicates a strong predisposition (90% at the age of 70 years) or a susceptibility to the occurrence of prostate cancer, and, a family having been analyzed, a link has been made between the presence of this allele and the occurrence of prostate cancer.

The present invention likewise relates to DNA sequences situated in the regions defined by the markers:

D1S235 and D1S2842, preferably D1S2678 and D1S321, on chromosome 1

D1S252 and D1S218, preferably D1S498 and D1S196, on chromosome 1

D2S155 and D2S339, preferably D2S2319 and D2S163, on chromosome 2

D4S405 and D4S1543, preferably D4S2978 and D4S3018, on chromosome 4

D5S2002 and D5S2013, preferably D5S393 and D5S436, on chromosome 5

D8S264 and D8S1819, preferably D8S262 and D8S561, on chromosome 8

D10S547 and D10S208, preferably D10S191 and D10S197 on chromosome 10

D11S898 and D11S1320, preferably D11S908 and D11S934, on chromosome 11

D13S1290 and D13S281, preferably D13S1283 and D13S1300, on chromosome 13 and implicated in prostate cancer, as well as the equivalent sequences.

"Equivalent sequences" are understood as designating the sequences coding for the same proteins taking account of the degeneracy of the genetic code, as well as the sequences hybridizing with the previous sequences and, finally, the sequences coding for equivalent proteins.

In what will follow, the previous DNA sequences will be called "sequences involved in prostate cancer" or "gene involved in prostate cancer", whether they are normal or pathological sequences.

"Equivalent protein" will be understood as designating a protein having the same type of function, especially the suppressor function, but which could have, with respect to the natural protein, certain modifications and which could, in particular, be a deleted, truncated, elongated or chimeric protein, and/or having undergone mutations, especially point mutations, provided that it retains the same type of activity.

Owing to the preceding developments, it is possible to localize genes implicated in prostate cancer.

The localization of the gene(s) of familial prostate cancer can be conducted using the data of the integrated CEPH/Genethon map of the human genome.

Once a candidate region has been defined, it is necessary to have access to the genome fragment covering the interval where the desired gene is situated. This step proceeds by establishment of a physical map, namely the covering of the region with a group of cloned and ordered fragments. Today, owing to the data of the integrated CEPH/Genethon map of the human genome, approximately 80% of the genome is covered by clones of YACs (Yeast Artificial Chromosomes), subcloned in BACs (Bacterial Artificial Chromosomes) whose localization on the chromosomes is made by the intermediary of polymorphic and genetically ordered markers (Chumakov et al., 1995). This physico-genetic map allows considerable time to be gained, especially by the use of exhaustive sequencing of the regions of interest.

In addition, cDNA banks specific to normal human prostate tissue, to benign hypertrophy of the prostate, and to prostate cancer, have been produced. The sequencing of these cDNAs and the direct comparison of the data obtained with the exhaustive sequencing data of the regions of interest, allow the potential coding sequences to be identified rapidly. The data available from public banks, especially from HGS-TIGR (Adams et al., 1995) are likewise used in this comparative strategy.

For the actual identification of the predisposition gene, a selection is made, starting from very informative families for a given localization, of those having an inherited anomaly (mutation, deletion . . . ) within the whole of the identified coding sequences.

The present invention likewise relates to inhibition/blocking or replacement therapies, according to whether the gene involved has true oncogenic characteristics or suppressor characteristics.

The markers demonstrated in the context of the present invention allow the isolation of genes which can be of one or the other family.

When the gene is an oncogene, it is advisable to block the expression of this gene or its expression product. If the promoter sequence of this oncogene is responsible for deregulation, this sequence could be used to induce a suicide strategy.

On the contrary, in the case where the gene is a suppressor gene, its link with prostate cancer can come from the fact that this gene is not expressed, is insufficiently expressed or is expressed in an abnormal form which does not allow it to fulfil its suppressor role. It is thus expedient to overcome the shortage of expression products of this gene by a therapy called "replacement therapy".

The present invention likewise relates to a replacement therapy which could be carried out by gene therapy, that is to say by introducing the nucleotide sequences and/or corresponding genes with the elements which allow their expression in vivo, in the case where the suppressor gene is insufficiently expressed for example, or alternatively when it is expressed in an abnormal form.

The principles of gene therapy are known. It is possible to use viral vectors, for example those based on adenoviruses, retroviruses, poxviruses or herpesviruses. Most of the time, these viruses are used in defective form and, generally speaking, with or without integration into the cell genome. It is likewise possible to provide for non-viral, that is to say synthetic, vectors, which mimic the viral sequences or alternatively which are formed by the naked DNA or RNA according to the technique developed especially by VICAL.

In the majority of cases, it will be necessary to provide for targeting elements ensuring a tissue-specific or organ-specific expression so as to be able to limit the expression zones of the proteins which remain involved in oncogenesis; it is even worthwhile, in certain cases, to have transitory expression vectors or at least controlled expression vectors which could be blocked when this was necessary.

The present invention thus relates to the vectors such as described above, it likewise relates to cells transformed by an expression vector such as described above.

The transformed cells can equally well be prokaryotic cells such as bacterial cells, eukaryotic cells (yeasts, mammalian cells—especially murine cells—or insect cells), of which it will be seen that they can likewise serve as a screening model.

The present invention likewise relates to the proteins which can be obtained by culture of transformed cells.

Among these proteins, proteins corresponding to the expression of the normal gene in order to overcome the expression of an abnormal protein such as in the context of replacement therapies with p53 can appear.

The present invention likewise relates, by way of medicament, to a compound ensuring the cellular expression of at least one of the above nucleotide sequences when it is a suppressor gene or, on the contrary, ensuring the inhibition of the cell expression of at least one sequence such as described above, when this has an oncogenic function.

For example, it is possible to provide for other approaches to gene therapy; it is possible to provide for strategies for blocking the expression of oncogenic sequences with the aid of sense or anti-sense strategies, that is to say being able to block the expression of the corresponding genes or, on the contrary, acting upstream to favor the said expression.

It is likewise possible to provide for a direct replacement strategy by supply of the corresponding proteins or, when the expression leads to an abnormal protein, an inactivation strategy by inhibitory antibodies.

Finally, it is possible to provide for the use of non-protein molecules whose effect will be to activate the suppressor gene or to mimic the action of its expression product or alternatively to inhibit the oncogene or alternatively to block the action of its expression product.

The demonstration of these products can easily be carried out, especially on the modified cell cultures which have been described above. It will suffice, in fact, to introduce the products to be tested into the cell cultures and to detect the appearance of the oncogenesis phenomenon or on the contrary the regression of the oncogenesis phenomenon.

In the strategies which involve the use of nucleic acids, DNA or RNA, the products are, of course, elaborated as a function of the sequences which are described.

The present invention likewise relates to the use of the above medicaments as anticancer agents.

The invention likewise relates to the use of the transformed cells as a model allowing, especially, the selection of anticancer products or in order to demonstrate the risks presented by certain oncogenic compounds.

Other characteristics and details of employing the present invention will be inferred from reading the examples which follow.

EXAMPLE I—Recruitment

The sole criterion of inclusion retained in the genetic analysis study of familial prostate cancer is the presence of at least two members affected by prostate cancer.

The genealogical and clinical information were recorded on a relational database management system (Medisys). The genealogical tree of each family was produced with the aid of the Ped Draw software.

Among all the families included in the study (Table 1), only families having (i) at least 3 cases of clinically confirmed prostate cancer, (ii) of which it was possible to sample at least two cases (Table 2) were retained for the genetic analysis.

EXAMPLE 2—Method of typing of human genomic DNA

A) Taking of Blood and Clinical Confirmation

The peripheral blood of subjects of families having an increased risk for prostate cancer included in the genetic study is taken at the same time;
1. in a dry tube for carrying out serum collection and the analysis of the PSA (IRMA-PSA-RIACT kit, Cis Bio International, Saclay, France)
2. in an EDTA tube to extract DNA (cf. protocol below)
3. in a heparinized tube for culture and immortalization of the lymphocytes and establishment of the lymphocyte collection (Valeri et al., 1996).

Clinical confirmation: in order to confirm the pathology of prostate cancer of the affected subjects mentioned, we proceed to:
(i) a systematic determination of the PSA by taking as a reference the normal value indicated by the supplier
(ii) the recording and archiving of a copy of the anatomo-pathological and/or operating report deciding the stage and/or tumour grade.

Extraction of DNA in an EDTA tube

Centrifuge at 2000 rpm for 10 min. aspirate the plasma, lyse in 50 ml final volume with a red blood cell lysis solution (TRIS $10^{-2}$M pH 7.6,. NaCl $10^{-2}$M; MgCl$_2$ $5\times10^{-3}$M), stir by slow turning and centrifuge at 3000 rpm for 5 min, resuspend the cell pellet in a 50 ml final volume of red blood cell lysis solution, centrifuge at 3000 rpm for 5 min.

The extraction is carried out volume for volume. Add to the white blood cells pellet 1 volume of white blood cell lysis solution (TRIS $10^{-2}$M pH=7.6; NaCl $10^{-2}$M; EDTA $10^{-2}$M, pH=8, SDS 0.2%, proteinase K 0.02%) following the treatment of the tubes with the red blood cell lysis solution, stir so as to separate the pellet and leave for one night at 42° C. with stirring. Extract the DNA in 1 volume of phenol/chloroform/isoamyl alcohol, stir for 15 min and centrifuge for 2 min at 700×g. Repeat this operation once. Resuspend in one volume of chloroform/isoamyl alcohol solution, stir for 15 min and centrifuge for 2 min at 700×g, Precipitate by addition of one volume of isopropanol. After recovery of the precipitate, wash in 70 ethanol and redissolve in 10-1 TE. The DNA are stored at −80° C. at a concentration of 200 ng/µl.

B) Genotyping

This phase has the aim of determining the allelic profile of the subjects studied for the different microsatellite markers tested. This is carried out on the constitutional DNA of subjects selected within informative families (see above), for highly polymorphic microsatellite markers (Dib et al., 1996). The DNA of the individuals C.E.P.H. No. 134702 and No. 88415, whose allelic profile is completely known for all markers tested, were used as controls. Two complementary methods of genotyping were employed in this study. The first method called the classical method is based on the Southern blot principle with detection by chemoluminescence, then manual reading of the allelotypes. The second method uses the principle of genotyping developed by Applied Biosystem Inc. on the ABI 377 automatic sequencer, called the Genscan procedure.

Genotyping, Genethon method

The different technical phases were described above (Vignal et al., 1993; Valeri, 1996, Valeri et al., 1996) and are summarized as follows:

Polymerase Chain Reaction (PCR)

The DNA is diluted in 10-1 TE to 6 ng/µl. The amplification technique used is based on "hot start" starting of the reaction, and integrates the elongation phase during temperature transitions (55° C.–94° C.) of each cycle.

Coprecipitation for 16 markers

The PCR products of 16 markers were coprecipitated together. The DNA is then resuspended with 5 µl of 10-1 TE per well, then 12.5 µl of formamide blue (denaturing colorant).

Electrophoresis on sequence gel and transfer

For each DNA sample, the PCR products of 16 "pooled" markers were separated by electrophoresis on highresolution sequence gel (6% acrylamide), then transferred to nylon membrane. The series of markers perfected by the team of Jean Weissenbach were divided so as to avoid the overlapping of DNA bands (Vignal et al., 1993; Gyapay et al., 1994; Dib et al., 1996).

Hybridization

A first hybridization of each membrane obtained was carried out with a non-specific poly-AC probe with the aim of estimating, after detection, the overall results of the genotyping for the series of 16 markers loaded on the gel. In order to allow the reading of the allelic profiles of the individuals, a specific hybridization was then carried out for each microsatellite marker considered. One of the specific primers of the marker considered, of the same sequence as those which served for the PCR, was used as a probe. An elongation was likewise carried out at the transferase terminal.

Reading of the allelic profiles

This was carried out by comparing the alleles of each individual with those of the controls C.E.P.H. No. 134702 and No. 88415 whose allelic profile is completely known for all of the markers tested.

Genotyping. ABI-Genscan method

The ABI-Genscan genotyping method was carried out using the PRISM Genotyping System of Applied Biosystem Inc. (ABI).

The PCR primers contained in the linkage mapping set of ABI allow the amplification of microsatellite markers separated by approximately 10 cM. The loci analysed were selected from the Genethon genetic map (Dib et al., 1996), according to their position, their degree of heterozygosis, and the quality of the amplification by PCR. The markers of the linkage mapping set of ABI are organized into 28 sample groups of 9 to 17 pairs of primers. The primers in 5' are labelled with a fluorochrome (6-FAM, HEX or TET). The PCR products corresponding to the genetic markers studied will be identified individually according to their molecular weight. The PCR reactions and the electrophoreses were carried out according to the protocols recommended by the suppliers. The electrophoreses and the detection of the markers were carried out on ABI-377 DNA sequencers equipped with GeneScan 2.0 software which carries out data acquisition. The data were then analysed with the aid of the Genotyper 1.1 software.

C) Genetic analysis

Arithmetical models

The disease was modelled as a dominant autosomal disease with 6 penetrance classes. The four first classes correspond to the following age brackets for the men: before 40; 40 to 55; 55 to 70; after 70 years, with the following respective penetrances, equally for the susceptible heterozygous and homozygous genotypes: 0.01, 0.1, 0.5, 0.9. These data were calculated from Carter curves. The two last classes correspond to the sick people (penetrances=1) and to the women (penetrances=0).

In the general population, the proportion of phenocopies is approximately 90%. There is no means of estimating the statistical bias due to the recruitment of the families studied. We have thus constantly used the two following models in parallel.

For the first, the proportion of phenocopy was fixed at a constant value of 0.01, coded as the penetrance of the non-susceptible genotype, in all the classes of penetrance (except the women). The second model employs a variable proportion of phenocopy, equal to 10% of the penetrance of the susceptible genotype for each class except the first, or 0.01, 0.01, 0.05, 0.09, 0.1 respectively.

The first model is thus more stringent with respect to the robustness of a possible genetic link.

Simulation analysis

Previously to the analysis, simulations were carried out with the aid of the fastlink program and associated programs (Weeks et al., 1990 and Schaffer, to appear).

The results allowed it to be concluded that a sub-total of 11 to 17 families was sufficient to establish a genetic link. According to the cases, several such sub-assemblies were employed, several families being common to all.

Linkage analysis at 2 points

The lod scores at 2 points, which are parametric, of all the marker-disease and marker-marker pairs were calculated with the mlink program for the whole.

Fastlink version 3.OP (Lathrop et al., 1984; Cottingham et al., 1993; Schaffer et al., 1994).

The analysis of the lod marker-marker scores allows possible errors to be detected if the results are far too different from the genetic reference maps (Genethon).

Multipoint linkage analysis

We used the Genehunter program (Kruglyak et al., 1996), which allows the parametric lod scores to be calculated simultaneously, and non-parametric statistics, named NPL score by the authors, analogous to extended sib-pair type statistics. The program also calculates the value of the p-value corresponding to the NPL score, as well as the informativeness of the markers on the map.

For the two types of statistics, a lod score value equal to x indicates a probability of (10 to the power of x) against 1 for the existence of a genetic link.

In addition, Genehunter reconstitutes the most probable haplotypes, presented on genealogical trees (postscript format).

The settings of the program were: max bits=20, skip large off.

These two options allow the program to analyse complex genealogies, if necessary simplifying them, with a minimal loss of information.

Results

The results relating to chromosome 1, 2, 4, 5 and 13 are detailed below.

For chromosome 13, Table 3 shows the lod scores at 2 points between the disease and the markers on a sub-total of selected families according to a positive individual lod score. The value of 3.49 obtained suffices per se to validate a genetic link with the marker D13S1300. The curve of FIG. 14 shows the variation of the lod score on a map of 6 markers centered on D13S170. The value higher than 5 proves that a gene involved in familial prostate cancer is found in the region situated between the markers D13S153 and D13S159, probably between D13S156 and D13S265, or a space of approximately 13 cM. These results correspond to the first genetic model presented above, those corresponding to the second model confirm them.

Finally a finer analysis according to the above methods has allowed the curve of FIG. 15 to be established: variation of the lod score on a map of 8 markers centered on D13S265. These results indicate that the gene mentioned above is probably found in the region between D13S1283 and D13S1300, or a space of approximately 4.6 cM.

For chromosome 1, region 1B, Table 4, showing the lod scores at 2 points between the disease and the markers in the total population of approximately about forty families, indicates an lod score 2.33, which validates a genetic link with the marker D1S2785. The curve of FIG. 9 shows the variation of the lod score on a map of 3 markers centered on D1S2785. The value higher than 3.35 proves that a gene involved in familial prostate cancer is found in the region between D1S678 and D1S321, or a space of approximately 17 cM. Finally, a heterogeneity analysis (multipoint lod score and M-test - Ott, 1986-) was conducted on a sub-group of 9 families, in which the age of diagnosis of the members affected in the last generation is lower than 60 years. The chi-2 obtained, of 16.25, under the heterogeneity hypothesis as a function of age, as well as a multipoint lod score of 3.31, a 2-point lod score of 2.17 for the marker D1S2785 suggest that the gene demonstrated above is involved in patients diagnosed early.

For chromosome 5, the curve of FIG. 13 shows the variation of the lod score on a map of 8 markers centered on D5S2011. The value greater than 7 proves that a gene involved in familial prostate cancer is found in the region situated between the markers D5S2002 and D5S2013, or a space of approximately 15.1 cM, and more probably between D5S393 and DSS436, or a space of approximately 6.4 cM.

For chromosome 2, Table 5, showing the lod scores at 2 points between the disease and the markers on the total population of approximately about fifty families, indicates an lod score 3.17, which validates a genetic link with the marker D2S163. The curve of FIG. 11 shows the variation of the lod score on a map of 5 markers, centered on D2S2382. These results indicate that a gene involved in the familial prostate cancer is probably found in the region between D2S2319 and D2S163, or a space of approximately 8.1 cM.

For chromosome 4, Table 6 shows the lod scores at 2 points between the disease and the markers on the total population of approximately about fifty families. The value of 2.49 indicates a probable genetic link with the marker D4S398. The curve of FIG. 12 shows the variation of the lod score on a map of 5 markers, centered on D4S398. The value higher than 3.3 indicates that a gene involved in familial prostate cancer is probably found in the region situated between the markers D4S2978 and D4S3018, or a space of approximately 9.7 cM.

TABLE 1

Total number of families included in the study as a function of the number of living persons affected by prostate cancer and of the total number of prostate cancers (PCA) present in the family

| Number of living PCa per family | 0 | 1 | 2 | 3 | 4 | 5 | 6 | 7 | |
|---|---|---|---|---|---|---|---|---|---|
| Number of PCa per family | | | | | | | | | |
| 2 | 166 | 210 | 141 | | | | | | 517 |
| 3 | 38 | 68 | 51 | 13 | | | | | 170 |
| 4 | 6 | 16 | 14 | 11 | 5 | | | | 52 |
| 5 | 0 | 4 | 1 | 4 | 1 | 1 | | | 11 |
| 6 | 1 | 2 | 0 | 1 | 1 | 0 | 0 | | 5 |
| 7 | 0 | 0 | 0 | 0 | 0 | 1 | 0 | 0 | 1 |
| | 21 | 300 | 207 | 29 | 7 | 2 | 0 | 0 | 756 |
| | 1 | | | | | | | | |

TABLE 2

Total number of informative families for the analysis of links as a function of the number of living persons affected by prostate cancer and of the total number of prostate cancers present in the family

| Number of living PCa per family | 0 | 1 | 2 | 3 | 4 | 5 | 6 | 7 | |
|---|---|---|---|---|---|---|---|---|---|
| Number of PCa per family | | | | | | | | | |
| 2 | 0 | 0 | 0 | | | | | | 0 |
| 3 | 0 | 2 | 52 | 13 | | | | | 66 |
| 4 | 0 | 0 | 14 | 11 | 5 | | | | 30 |
| 5 | 0 | 0 | 1 | 4 | 1 | 1 | | | 7 |
| 6 | 0 | 0 | 0 | 1 | 1 | 0 | 0 | | 2 |
| 7 | 0 | 0 | 0 | 0 | 0 | 1 | 0 | 0 | 1 |
| | 0 | 2 | 66 | 29 | 7 | 2 | 0 | 0 | 106 |

TABLE 3

Two-point lod scores between different markers and the disease as a function of the recombination level (theta), on a positively linked selected population of families

| theta | 0.0 | 0.001 | 0.01 | 0.05 | 0.1 | 0.2 | 0.3 | 0.4 |
|---|---|---|---|---|---|---|---|---|
| D13S1264 | 1.59 | 1.59 | 1.57 | 1.46 | 1.28 | 0.88 | 0.48 | 0.16 |
| D13S1290 | 1.33 | 1.34 | 1.38 | 1.44 | 1.35 | 0.98 | 0.56 | 0.20 |
| D13S1283 | 0.12 | 0.17 | 0.53 | 1.13 | 1.24 | 0.95 | 0.50 | 0.14 |
| D13S1230 | 1.91 | 1.91 | 1.88 | 1.73 | 1.49 | 0.96 | 0.48 | 0.14 |
| D13S1234 | 0.93 | 0.93 | 0.92 | 0.87 | 0.78 | 0.55 | 0.31 | 0.09 |
| D13S265 | 3.39 | 3.38 | 3.35 | 3.09 | 2.66 | 1.72 | 0.86 | 0.23 |
| D13S1300 | 3.49 | 3.48 | 3.39 | 2.99 | 2.50 | 1.57 | 0.78 | 0.22 |
| D13S281 | 2.31 | 2.31 | 2.25 | 2.00 | 1.68 | 1.06 | 0.53 | 0.15 |
| D13S167 | 1.78 | 1.79 | 1.88 | 1.95 | 1.79 | 1.24 | 0.65 | 0.18 |

TABLE 4

Two point lod scores between different markers and the disease as a function of the recombination level (theta), on a total population of 46 families

| theta | 0.0 | 0.001 | 0.01 | 0.05 | 0.1 | 0.2 | 0.3 | 0.4 |
|---|---|---|---|---|---|---|---|---|
| D1S235 | −0.25 | −0.25 | −0.20 | −0.03 | 0.09 | 0.15 | 0.10 | 0.03 |
| D1S2678 | −0.32 | −0.31 | −0.27 | −0.12 | −0.01 | 0.07 | 0.06 | 0.02 |
| D1S2785 | 2.33 | 2.33 | 2.29 | 2.09 | 1.81 | 1.19 | 0.62 | 0.19 |
| D1S321 | −0.94 | −0.93 | −0.86 | −0.61 | −0.38 | −0.11 | −0.01 | 0.01 |
| D1S2842 | 0.65 | 0.65 | 0.67 | 0.68 | 0.65 | 0.48 | 0.27 | 0.09 |

TABLE 5

Two-point lod scores between different markers and the disease as a function of the recombination level (theta), on a total population of about fifty families

| theta   | 0.0   | 0.001 | 0.01  | 0.05  | 0.1   | 0.2  | 0.3  | 0.4  | Max  |
|---------|-------|-------|-------|-------|-------|------|------|------|------|
| D2S2237 | −3.9  | −3.78 | −2.94 | −1.13 | −0.2  | 0.36 | 0.31 | 0.1  | 0.36 |
| D2S155  | −0.67 | −0.58 | 0.06  | 1.25  | 1.63  | 1.37 | 0.73 | 0.18 | 1.63 |
| D2S2319 | −6.27 | −6.03 | −4.42 | −1.14 | 0.43  | 1.21 | 0.9  | 0.35 | 1.21 |
| D2S2382 | −2.33 | −2.17 | −1.09 | 1.04  | 1.85  | 1.81 | 1.08 | 0.33 | 1.85 |
| D2S163  | 2.07  | 2.13  | 2.55  | 3.17  | 3.14  | 2.36 | 1.33 | 0.44 | 3.17 |
| D2S339  | −3.54 | −3.4  | −2.4  | −0.43 | 0.46  | 0.85 | 0.59 | 0.19 | 0.85 |

TABLE 6

Two-point lod scores between different markers and the disease as a function of the recombination level (theta), on a total population of about fifty families

| theta   | 0.0  | 0.0   | 0.01  | 0.05  | 0.1  | 0.2  | 0.3  | 0.4  | Max  |
|---------|------|-------|-------|-------|------|------|------|------|------|
| D4S3001 | −3   | −3.25 | −2.34 | −0.44 | 0.43 | 0.76 | 0.49 | 0.15 | 0.76 |
| D4S1581 | −2   | −1.54 | −1.09 | −0.04 | 0.46 | 0.6  | 0.37 | 0.1  | 0.6  |
| D4S405  | −2   | −1.9  | −1.03 | 0.84  | 1.62 | 1.61 | 0.94 | 0.28 | 1.62 |
| D4S2996 | −0   | −0.17 | 0.25  | 1.03  | 1.25 | 1.02 | 0.55 | 0.16 | 1.25 |
| D4S2978 | −3   | −3.14 | −2.11 | −0.04 | 0.84 | 1.06 | 0.65 | 0.2  | 1.06 |
| D4S398  | 0.5  | 0.62  | 1.23  | 2.28  | 2.49 | 1.93 | 1.03 | 0.3  | 2.49 |
| D4S3004 | 1.8  | 1.82  | 2.06  | 2.35  | 2.2  | 1.51 | 0.76 | 0.21 | 2.35 |
| D43018  | −0   | −0.37 | 0.42  | 1.95  | 2.44 | 2.08 | 1.18 | 0.35 | 2.44 |
| D4S1543 | −2   | −1.84 | −1.36 | −0.28 | 0.27 | 0.53 | 0.37 | 0.13 | 0.53 |
| D4S3042 | −4   | −3.69 | −2.75 | −0.82 | 0.09 | 0.52 | 0.35 | 0.11 | 0.52 |

REFERENCE

Adams, et al. Initial assessment of human gene diversity and expression patterns based upon 83 million nucleotides of cDNA sequence. Nature 1995; 377 supplt:3–174.

Carter B. S., Bova S. G., Beaty T. H. et al. Hereditary prostate cancer epidemiologic and clinical features. J Urol 1993;150:797–802.

Chumakov I. M., Rignault P., Le Gall 1. et al. A YAC contig map of the human genome. Nature 1995; 3 77 Supplt: 175–183.

Cottingham R. W. Jr., Idury R. M., and. Schaffer A. A. Faster Sequential Genetic Linkage Computations, American Journal of Human Genetics 1993; 53:252–263.

Dib C., Faure S., Fizames C. et al. A comprehensive genetic map of the human genome based on 5,264 microsatellites. Nature 1996; 380:III–V.

Gyapay G., Morissette J., Vigal A. et al. The 1993–1994 Genethon human genetic linkage map. Nat Genetics 1994; 7:246.

Kruglyak L., Daly M. J., Reeve-Daly M. P., and Lander E. S. "Parametric and Nonparametric Linkage Analysis: A Unified Multipoint Approach". American Journal of Human Genetics 1996; 58:1347–1363.

Lathrop G. M., Lalouel J. M., Julier C., Ott J. Strategies for multilocus linkage analysis in humans. Proc Natl Acad Sci USA 1984; 81:3443–3446.

Mc Whorter W. P., Hernandez A. D., Meikle A. W. et al. A screening study of prostate cancer in high risk families. J Urol 1992;148:826–828.

Ott, J. Linkage probability and its approximate confidence interval under possible heterogeneity. Genet. Epidemiol. Suppl. 1986; 1, 251–257.

Schaffer A. A., Gupta S. K., Shriram K., and Cottingham R. W, Jr. Avoiding Recomputation in Linkage Analysis, Human Heredity 1994; 44: 225–237.

Schaffer A. A. Faster Linkage Analysis Coutations for Pedigrees with Loops or Unused Alleles. Human Heredity, to appear.

Steinberg G. D., Carter B. S., Beaty T. H. et al. Family history and the risk of prostate cancer, The prostate 1990;17, 337–347.

Valeri A., Berthon P., Fournier G. el al. Etude PROGENE, projet francais d'analyse genetique du CaP familial: recrutement et analyse. Progres en Urologic 1996; 6:226–235.

Vignal A., Gyapay G., Hazan 1. et al. Nonradioactive multiplex procedure for genotyping of microsatellite markers. Meth Mol Genetics 1993; I:211–221.

Weeks D. E., Ott J., Lathrop G. M. SLINK a general simulation program for linkage analysis. Am J Hum Genet 1990; 47: A204 (abstr).

What is claimed is:

1. A method for detecting a predisposition or susceptibility to prostate cancer in an individual, said method comprising detecting, in a biological sample from the said individual, alleles of the markers linked to the occurrence of prostate cancer in his family as indicative of the presence of a predisposition or susceptibility to prostate cancer, these markers being selected from the microsatellite markers included in one of the groups of markers consisting of: D1S235, D1S2678, D1S2785, D1S321, D1S2842 of chromosome 1, D1S252, D1S498, D1S305, D1S484, D1S196of chromosome 1, D2S155, D2S325, D2S2242, D2S2321, D2S317, D2S2319, D2S2382, D2S2249, D2S163, D2S339 of chromosome 2, D4S405, D4S2974, D4S2996, D4S428, D4S2978, D4S3019, D4S1592, D4S398, D4S2987, D4S3004, D4S3018, D4S392, D4S1543 of chromosome 4, D5S2002, D5S2117, D5S393, D5S414, D5S2011, D5S2017, D5S436, D5S2090, D5S2013 of chromosome 5, D11S898, D11S927, D11S908, D11S1345, D11S934, D11S1320 of chromosome 11, D13S1290, D13S1283, D13S1230, D13S1234, D13S265, D13S1300, D13S281 of chromosome 13 and all polymorphic markers localized in the regions situated between the above markers and determining whether said detected alleles are indicative of a predisposition or susceptibility to prostate cancer.

2. A method according to claim 1, wherein the marker whose allele is detected is localized on chromosome 1 in the region situated between the markers D1S2678 and D1S321.

3. A method according to claim 1, wherein the marker whose allele is detected is localized on chromosome 1 in the region situated between the markers D1S498 and D1S196.

4. A method according to claim 1, wherein the marker whose allele is detected is localized on chromosome 2 in the region situated between the markers D2S2319 and D2S163.

5. A method according to claim 1, wherein the marker whose allele is detected is localized on chromosome 4 in the region situated between the markers D4S2978 and D4S3018.

6. A method according to claim 1, wherein the marker whose allele is detected is localized on chromosome 5 in the region situated between the markers D5S393 and D5S436.

7. A method according to claim 1, wherein the marker whose allele is detected is localized on chromosome 11 in the region situated between the markers D11S908 and D11S934.

8. A method according to claim 1, wherein the marker whose allele is detected is localized on chromosome 13 in the region situated between the markers D13S1283 and D13S1300.

9. A method according to claim 1, wherein the presence of said marker is detected by amplification of the region carrying said marker.

10. A method according to claim 9, wherein the amplification is carried out by PCR.

* * * * *